(12) United States Patent
Spaas et al.

(10) Patent No.: US 12,329,782 B2
(45) Date of Patent: Jun. 17, 2025

(54) MESENCHYMAL STEM CELLS FOR USE IN THE TREATMENT OF ATOPIC DERMATITIS

(71) Applicant: Boehringer Ingelheim Veterinary Medicine Belgium, Evergem (BE)

(72) Inventors: Jan Spaas, Evergem (BE); Glenn Pauwelyn, Evergem (BE); Stephanie Carlier, Evergem (BE); Sarah Broeckx, Evergem (BE)

(73) Assignee: Boehringer Ingelheim Veterinary Medicine Belgium, Evergem (BE)

( * ) Notice: Subject to any disclaimer, the term of this patent is extended or adjusted under 35 U.S.C. 154(b) by 110 days.

(21) Appl. No.: 17/857,495

(22) Filed: Jul. 5, 2022

(65) Prior Publication Data

US 2023/0014698 A1 Jan. 19, 2023

(30) Foreign Application Priority Data

Jul. 8, 2021 (EP) .................................... 21184480

(51) Int. Cl.
*A61K 35/28* (2015.01)
*A61P 17/04* (2006.01)

(52) U.S. Cl.
CPC .............. *A61K 35/28* (2013.01); *A61P 17/04* (2018.01)

(58) Field of Classification Search
CPC .. A61K 35/28; A61K 2035/124; A61K 35/14; A61P 17/04; A61P 37/08
See application file for complete search history.

(56) References Cited

FOREIGN PATENT DOCUMENTS

| CA | 3127868 A1 | 8/2020 |
|---|---|---|
| KR | 20140076198 A | 6/2014 |
| WO | 2014053418 A2 | 4/2014 |
| WO | 2014053420 A2 | 4/2014 |
| WO | 2014203269 A | 12/2014 |
| WO | 2017144552 A1 | 8/2017 |
| WO | 2020182935 A1 | 9/2020 |
| WO | 2021226455 A1 | 11/2021 |

OTHER PUBLICATIONS

USP 797: Pharmaceutical Compounding—Sterile Preparations (2008). (Year: 2008).*
Voga et al. (Front. Vet. Sci. 7: 1-20. 2020). (Year: 2020).*

(Continued)

*Primary Examiner* — Tracy Vivlemore
*Assistant Examiner* — Thomas R. Amick
(74) *Attorney, Agent, or Firm* — Hodgson Russ LLP

(57) ABSTRACT

Mesenchymal stem cells (MSCs) or a pharmaceutical composition comprising a therapeutically effective amount of MSCs can be used in the treatment of atopic dermatitis (AD) in canines and felines. In a second aspect, the MSCs or a pharmaceutical composition comprising a therapeutically effective amount of MSCs can be used as an immunomodulating agent during the acute and/or the chronic phase of the AD inflammatory reaction in canines and felines diagnosed with or suffering from atopic dermatitis. In a last aspect, a pharmaceutical composition comprises peripheral blood-derived MSCs.

18 Claims, 2 Drawing Sheets

(56) References Cited

OTHER PUBLICATIONS

González-González, Alberto et al. "Mesenchymal stem cells secretome: The cornerstone of cell-free regenerative medicine." World journal of stem cells vol. 12, 12 (2020): 1529-1552. (Year: 2020).*

Enciso, Nathaly et al. Multidose intramuscular allogeneic adipose stem cells decrease the severity of canine atopic dermatitis: A pilot study.âVeterinary world vol. 12,11 (2019): 1747-1754 (Year: 2019).*

Kim, Ung, et al. "Homing of adipose-derived stem cells to radiofrequency catheter ablated canine atrium and differentiation into cardiomyocyte-like cells." International journal of cardiology 146.3 (2011): 371-378 (Year: 2011).*

Lin, Ching-Shwun, Guiting Lin, and Tom F. Lue. "Allogeneic and xenogeneic transplantation of adipose-derived stem cells in immunocompetent recipients without immunosuppressants." Stem cells and development 21.15 (2012): 2770-2778 (Year: 2012).*

Przdka, Przemysław et al. "The Role of Mesenchymal Stem Cells (MSCs) in Veterinary Medicine and Their Use in Musculoskeletal Disorders." Biomolecules vol. 11,8 1141. Aug. 2, 2021 (Year: 2021).*

Marsella, R., Segarra, S., Ahrens, K et al. Topical treatment with Sphingolipids and Glycosaminoglycans for canine atopic dermatitis. BMC Vet Res 16, 92 (2020)) (Year: 2020).*

Debosschere, Yves, et al. "Safety and immunomodulatory properties of equine peripheral blood-derived mesenchymal stem cells in healthy cats." Veterinary Immunology and Immunopathology 227 (2020): 110083 (Year: 2020).*

Daems, Robert, et al. "A feasibility study on the use of equine chondrogenic induced mesenchymal stem cells as a treatment for natural occurring osteoarthritis in dogs." Stem Cells International 2019.1 (2019): 4587594. (Year: 2019).*

Hoffman et al., "Concise Review: Stem Cell Trials Using Companion Animal Disease Models", Stem Cells, Apr. 12, 2016, pp. 1709-1729, vol. 34, Issue 7, Oxford University Press.

Ramos et al., "Canine atopic dermatitis attenuated by mesenchymal stem cells", Journal of Advanced Veterinary and Animal Research, Sep. 1, 2020, pp. 554-565, vol. 7, Issue 3, NIH.

Villatoro et al., "Allogeneic adipose-derived mesenchymal stem cell therapy in dogs with refractory atopic dermatitis: clinical efficacy and safety", VetRecord, Dec. 1, 2018, pp. 654-654, vol. 183, Issue 21, Wiley.

* cited by examiner

MESENCHYMAL STEM CELLS FOR USE IN THE TREATMENT OF ATOPIC DERMATITIS

CROSS-REFERENCE TO RELATED APPLICATIONS

This application claims priority to European Patent Application No. 21184480.8 filed Jul. 8, 2021, the disclosure of which is hereby incorporated by reference.

FIELD OF THE INVENTION

The present invention relates to mesenchymal stem cells for use in the treatment of canine and feline atopic dermatitis.

BACKGROUND

Atopic dermatitis (AD) in dogs or cats is defined as "a genetically-predisposed inflammatory and pruritic allergic skin disease with characteristic clinical features". It is associated most commonly with immunoglobulin E (IgE) antibodies specific for common environmental allergens such as house dust mites, grass and plant pollens. As dogs are most commonly kept as indoor pets, increased exposure to indoor allergens may have led to an increase in the prevalence of canine atopic dermatitis (cAD), which is currently estimated to be 10-15%.

In AD, there is an exacerbation of the immune response. While in the acute phase, there is a predominance of T helper 2 (Th2) lymphocytes with the release of proinflammatory cytokines, eosinophils, mast cell degranulation, and IgE. In the chronic phase, both a predominant T lymphocyte helper 1 (Th1) response and Th2 response are observed. Typically, a non-human animal with AD will exhibit pruritus of the face, ears, paws, extremities, and/or ventrum.

The currently recommended therapies for AD are oral-systemic use of immunosuppressants, such as corticosteroids, cyclosporin, and oclacitinib, associated with lotions, pipettes, and creams composed of moisturizers, emollients, and humectants to restore the skin barrier. For instance, orally administered glucocorticoids, such as prednisone, are often used to treat AD. However, steroid use can have numerous side effects, such as increased thirst, urination, hunger, and weight gain. Moreover, with prolonged use at high doses, steroids cause liver enlargement and increased liver enzymes, can cause high blood pressure and kidney disease, weakened muscles and ligaments, infections of the skin and bladder, and thinning of the skin and hair loss. As conventional immunomodulatory drug therapy such as glucocorticoids, or other novel therapies such as cyclosporine or monoclonal antibodies, are associated with numerous side effects that limit their long-term use, there is a need for more effective and safe therapeutic strategies' development.

Mesenchymal stem cells (MSCs) are multipotent adult stem cells that can be collected and isolated from a wide variety of tissues. MSCs can decrease the aggressiveness of several allergic diseases. MSCs have been known to interact with both innate and adaptive immune systems, which results in the suppressive effect on proliferation, differentiation and activation of immune cells.

Hence, mesenchymal stem cells (MSCs) have been proposed as a potential alternative for AD treatment because of their immunomodulatory properties, that could suppress the inflammation process of AD, slow down its progression on a very short term and even cause a reversion of the sustained damage. Several studies have investigated their safety and efficacy in the treatment of atopic dermatitis and showed very interesting results.

The majority of these studies are using autologous MSCs derived from adipose tissue or bone marrow (BM). In some cases however, the use of allogeneic or xenogeneic MSCs is a more favorable option as they offer a stringent selection of healthy and high quality stem cell donors. They allow the production of a ready-to-use product, avoiding the invasive harvesting and time-consuming cultivation of MSCs from each individual patient. Because of the relative low culture capacity of canine and feline MSCs, xenogeneic (e.g. human or equine) MSCs may advantageously be used, especially for commercial applications, such as for use in the treatment of atopic dermatitis (AD) in canines and felines. In addition, xenogeneic MSCs are free of transmissible species-specific pathogens.

Likewise, extraction of MSCs from bone marrow is an invasive and high-risk approach. Adipose tissue as source for MSCs is a safer, however still invasive, alternative.

In some cases, the use of native MSCs is a favorable option as they allow the production of a ready-to-use product, with minimum manufacturing and handling, thereby lowering cost of production.

There remains a need in the art for an improved use of MSCs to slow down the disease progression and/or even reverse the pathological condition of AD in the family of dogs and cats. The present invention targets at solving at least one of the aforementioned disadvantages.

SUMMARY OF THE INVENTION

The present invention and embodiments thereof serve to provide a solution to one or more of the above-mentioned disadvantages. To this end, the present invention relates to mesenchymal stem cells (MSCs) or a pharmaceutical composition comprising a therapeutically effective amount of MSCs for use in the treatment of atopic dermatitis (AD) in canines and felines. In embodiments, said MSCs are derived from blood, preferably peripheral blood. In embodiments, said MSCs are intravenously administered. In embodiments, said MSCs are native MSCs. In embodiments, said MSCs are xenogeneic MSCs. Preferred embodiments of the MSCs for use of the invention are disclosed herein.

In a second aspect, the present invention relates to MSCs or a pharmaceutical composition comprising a therapeutically effective amount of MSCs for use as an immunomodulating agent during the acute and/or the chronic phase of the AD inflammatory reaction in canines and felines diagnosed with or suffering from atopic dermatitis.

In a last aspect, the present invention relates to a pharmaceutical composition comprising peripheral blood-derived MSCs, said MSCs are animal-derived, and present in a sterile liquid.

DETAILED DESCRIPTION OF THE INVENTION

Figure 1A:
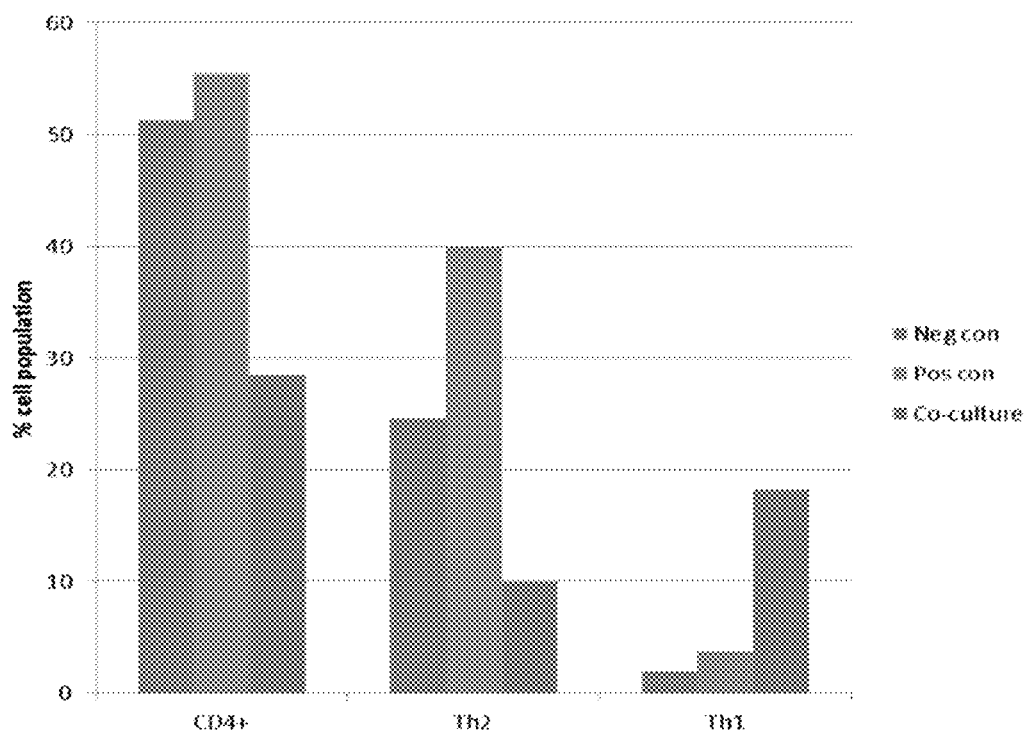
FIG. 1 shows an overview of the relative (FIG. 1A) and absolute (FIG. 1B) expression of CD4$^+$ T lymphocytes and Th1 and Th2 subsets within the proliferated PBMC population in the MLR-test for negative control, positive control and co-cultured samples.

The present invention concerns native MSCs for use in the treatment of atopic dermatitis in canines and felines, wherein said MSCs may be derived from blood, preferably peripheral blood. Blood is not only a non-invasive and painless source, but also simple and safe to collect and, consequently, easily accessible. In particular, MSCs may be derived from peripheral blood, preferably equine peripheral blood, which allows multiple MSC collections per year with minimal discomfort or morbidities for the donor animal.

Definitions

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The recitation of numerical ranges by endpoints includes all numbers and fractions subsumed within that range, as well as the recited endpoints.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any $\geq 3$, $\geq 4$, $\geq 5$, $\geq 6$ or $\geq 7$ etc. of said members, and up to all said members.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The terms "mesenchymal stem cells" or "MSCs" refer to multipotent, self-renewing cells that express a specific set of surface antigens and can differentiate into various cell types, including but not limited to adipocytes, chondrocytes, and osteocytes when cultured in vitro or when present in vivo.

The term "isolated", refers to both the physical identification and isolation of a cells from a cell culture or a biological sample, like blood, that can be performed by applying appropriate cell biology technologies that are either based on the inspection of cell cultures and on the characterization (and physical separation when possible and desired) of cells corresponding to the criteria, or on the automated sorting of cells according to the presence/absence of antigens and/or cell size (such as by FACS). In some embodiments, the terms "isolating" or "isolation" may comprise a further step of physical separation and/or quantification of the cells, especially by carrying out flow cytometry.

The term "in vitro" as used herein denotes outside, or external to, a body. The term "in vitro" as used herein should be understood to include "ex vivo". The term "ex vivo" typically refers to tissues or cells removed from a body and maintained or propagated outside the body, e.g., in a culture vessel or a bioreactor.

The term "passage" or "passaging" is common in the art and refers to detaching and dissociating the cultured (mesenchymal stem) cells from the culture substrate and from each other. For sake of simplicity, the passage performed after the first time of growing the cells under adherent culture conditions is generally referred to as "first passage" (or passage 1, P1). The cells may be passaged at least one time and preferably two or more times. Each passage subsequent to passage 1 is referred to with a number increasing by 1, e.g., passage 2, 3, 4, 5, or P1, P2, P3, P4, P5, etc.

The term "cell medium" or "cell culture medium" or "medium" refers to an aqueous liquid or gelatinous substance comprising nutrients which can be used for maintenance or growth of cells. Cell culture media can contain serum or be serum-free. The cell medium may comprise or be supplemented with growth factors.

The term "growth factor" as used herein refers to a biologically active substance which influences proliferation, growth, differentiation, survival and/or migration of various cell types, and may affect developmental, morphological and functional changes in an organism, either alone or when modulated by other substances. A growth factor may typically act by binding, as a ligand, to a receptor (e.g., surface or intracellular receptor) present in cells.

"Autologous" administration of MSCs in the present context refers to MSCs from a donor being administered to a recipient, wherein both recipient and donor are the same.

"Allogeneic" administration of MSCs in the present context refers to MSCs from a donor being administered to a recipient, wherein both recipient and donor are of the same species, but are not the same.

"Xenogeneic" administration of MSCs in the present context refers to MSCs from a donor being administered to a recipient, wherein the recipient and the donor are from different species.

"Native MSCs" in the context of the present invention refers to MSCs which have not been exposed to a stimuli environment, such as inflammatory mediators. As used herein, the "inflammatory environment" or "inflammatory condition" refers to a state or condition characterized by (i) an increase of at least one pro-inflammatory immune cell, pro-inflammatory cytokine, or pro-inflammatory chemokine; and (ii) a decrease of at least one anti-inflammatory immune cell, anti-inflammatory cytokine, or anti-inflammatory chemokine.

The term "anti-inflammatory", "anti-inflammation", "immunosuppressive", and "immunosuppressant" refers to any state or condition characterized by a decrease of at least one indication of localized inflammation (such as, but not limited to, heat, pain, swelling, redness, and loss of function) and/or a change in systemic state characterized by (i) a decrease of at least one pro-inflammatory immune cell, pro-inflammatory cytokine, or pro-inflammatory chemokine; and (ii) an increase of at least one anti-inflammatory immune cell, anti-inflammatory cytokine, or anti-inflammatory chemokine.

The "population doubling time" or "PDT" of current invention is to be calculated by the formula: $PDT=T/(\ln(N_f/N_i)/\ln(2))$, whereby T is the cell culture time (in days) to reach 80% confluency, $N_f$ is the final number of cells after cell detachment and whereby $N_i$ is the initial number of cells at time point zero.

By the term "anti-coagulant", it is meant a composition that can inhibit the coagulation of the blood. Examples of anticoagulants used in the present invention include EDTA or heparin.

The term "buffy coat" in this invention, is to be understood as the fraction of non-coagulated blood, preferably obtained by means of a density gradient centrifugation, whereby the fraction is enriched with white blood cells and platelets.

The term "blood-inter-phase" is to be understood as that fraction of the blood, preferably obtained by means of a density gradient, located between the bottom fraction, mainly consisting of erythrocytes and polymorphonuclear cells, and the upper fraction, mainly consisting of plasma. The blood-interphase is the source of blood mononuclear cells (BMCs) comprising monocytes, lymphocytes, and MSCs.

The term "suspension diameter" as used herein, is understood as the mean diameter of the cells, when being in suspension. Methods of measuring diameters are known in the art. Possible methods are flow cytometry, confocal microscopy, image cytometer, or other methods known in the art.

The term "therapeutically effective amount" is the minimum amount or concentration of a compound or composition that is effective to reduce the symptoms or to ameliorate the condition of a disease.

The term "treatment" refers to both therapeutic, prophylactic or preventive measures to reduce or prevent pathological conditions or disorders from developing or progressing.

"Canine Atopic dermatitis" (cAD) is a common condition among dogs with prevalence estimates reaching as high as 15%. The most common clinical sign of AD is pruritus (itching), which may be nonseasonal, seasonal, or nonseasonal with seasonal worsening. Beyond pruritus, the hallmarks of AD are chronic skin inflammation and recurrent secondary skin infections. Upon physical exam, these issues may appear as erythema (reddened skin), lichenification (thickened skin), hyperpigmentation (darkened skin), crusts (scabs), excoriations (erosions or ulcers caused by scratching), self-induced alopecia (hair loss), papules (small, raised areas of skin), and pustules (small, raised areas of skin filled with pus). Most affected areas of the body include the ventral tail, perineum, ventral abdomen, paws, carpal joints, tarsal joints, flexor aspects of the elbows, and head.

"Feline atopic dermatitis" (fAD) is a common condition among cats with prevalence estimates as high as 12.5%. As the function of IgE in the cat is not completely clarified, often the term "feline atopy like dermatitis" or "non-flea, non-food, hypersensitivity dermatitis (NFNFAD)" are also used. The most common clinical sign of AD is pruritus (itching), however, some cats present with only silent grooming. Pruritis and/or skin lesions can present seasonally or non-seasonally, depending on the responsible allergens. There is no typical pattern in the presenting symptoms, which complicates the diagnosis. Possible skin lesions can present as self-induced trauma, self-induced alopecia, excoriations, recurrent otitis externa, military dermatitis (small crusted papules), head and neck scratching and eosinophilic granuloma complex lesions. Non-cutaneous symptoms such as sneezing, coughing, conjunctivitis, diarrhea or vomiting have been reported. The most affected areas of the body include head, mouth, neck abdomen and trunk.

The terms "patient", "subject", "animal", or "mammal" are used interchangeably and refer to a mammalian subject to be treated. Preferably, the mammal is a canine or a feline, such as a dog or a cat.

"Canine" or "canines" in the present invention refers to dog-like carnivorans of the Canidae family. A member of this family is called a canid. There are three subfamilies found within the canid family, which are the extinct Borophaginae and Hesperocyoninae, and the extant Caninae. The Caninae are known as canines, and include domestic dogs, wolves, foxes, coyotes, jackals and other extant and extinct species.

"Feline" or "felines" in the present invention refers to cats of the Felidae family. A member of this family is also called a felid. The living Felidae are divided in two subfamilies: the Pantherinae and Felinae. Pantherinae includes five Panthera and two Neofelis species, while Felinae includes the other 34 species in ten genera, amongst which domestic cats, cheetahs, servals, lynx' and cougars.

"Mixed Lymphocyte Reaction (MLR)" assays are traditionally used to investigate if an external agent stimulates or suppresses T-cell proliferation. By using a MLR assay, the immunomodulatory properties of the MSCs can be investigated. For this MLR assay the responder T-cells are marked with a fluorescent dye which lights up green when it is exposed to a specific light frequency. These responder T-cells are then stimulated with a plant mitogen Concanavalin A (ConA) to induce or stimulate proliferation. ConA is an antigen-independent mitogen and can be used as an alternative T cell stimulus. This lectin is frequently used as a surrogate for antigen-presenting cells in T cell stimulation experiments. Concanavalin A irreversibly binds to glycoproteins on the cell surface and commits T cells to proliferation. This is a quick way to stimulate transcription factors and cytokine production. When the T-cells start to divide the dye is distributed over their daughter cells, so the dye is serially diluting with every cell division. Therefore, the amount of proliferation of T-cells can be measured by looking at the decrease of colour. Thus, to investigate the immunomodulatory properties of the MSCs, these MSCs are added to the stimulated responder T-cells and co-incubated for several days. Appropriate positive and negative controls are included to see if the test is performed successfully. At the end of the incubation period, the amount of T-cell proliferation is measured using flow cytometry, enabling to see whether or not the MSCs suppressed the T-cell proliferation.

DESCRIPTION

Corticosteroids are used for the symptomatic treatment of canine and feline AD. They have a powerful anti-inflammatory and anti-pruritic activity. Their activity, however, varies tremendously. There is no consistency in the individual reaction, not only in relation to the corticosteroid used, but also for the same corticosteroid. The effect is reduced over time and the doses required are increased. They are used topically or systemically. Topical application is of limited value because of the hair present on the body of the dog or cat (except perhaps as shampoos). As discussed above, systemic corticosteroids have significant side effects. The most common are polyuria-polydipsia, polyphagia, hepatomegaly, hypothalamuso-adrenal axis inhibition, drying of the skin and coat, and alopecia (iatrogenic Cushing's disease, which is often due to repeated injections of long-acting formulations). In addition, local immunosuppression may give rise to infections (pyoderma), demodicosis, and dermatophytosis.

Mesenchymal stem cells (MSCs) have been proposed for use in the treatment of inflammatory-related diseases because of their immunomodulatory properties. These immunomodulatory properties could suppress the exaggerated inflammation process of, amongst others, atopic dermatitis (AD), slow down its progression on a very short term and even cause a reversion of the sustained damage. Previous (canine) studies have investigated their safety and efficacy in the treatment of AD and showed very interesting results.

In an aspect, the invention relates to MSCs or a pharmaceutical composition comprising a therapeutically effective amount of MSCs for use in the treatment of AD in canines and felines or as a method for treating AD in canines and felines or for use in the preparation of a medicament for the treatment of AD in canines and felines.

Said canine may be any dog-like carnivoran of the Canidae family, preferably of the Caninae subfamily, more preferably a domestic dog (*Canis familiaris*). Said feline may be any cat-like carnivoran of the Felidae family, preferably of the Felinae subfamily, more preferably a domestic cat (*Felis catus*).

In an embodiment, said MSCs for use are native. Such native MSCs have not first in vitro been exposed to a stimulating agent, such as inflammatory mediators or an inflammatory environment. Such inflammatory environment refers to a state or condition characterized by (i) an increase of at least one pro-inflammatory immune cell, pro-inflammatory cytokine, or pro-inflammatory chemokine; and (ii) a decrease of at least one anti-inflammatory immune cell, anti-inflammatory cytokine, or anti-inflammatory chemokine. The use of native MSCs is sometimes a favorable option as they allow the production of a ready-to-use product, with minimum manufacturing and handling, thereby lowering cost of production.

By preference, the MSCs have a cell size between 10 µm to 100 µm, more preferably between 15 µm and 80 µm, more preferably between 20 µm and 75 µm, more preferably between 25 µm and 50 µm. In an embodiment, the MSCs for use according to the current invention are selected by size by means of a filter system, wherein the cells are run through a double filtration step using a 40 µm filter. Double or multiple filtration steps are preferred. The latter provides for a high population of single cells and avoids the presence of cell aggregates. Such cell aggregates may cause cell death during the preservation of the cells by freezing and may all have an impact on further downstream applications of the cells. For instance, cell aggregates may higher the risk of the occurrence of a capillary embolism when administered intravenously.

The majority of previous published studies are using autologous or allogeneic MSCs derived from adipose tissue or bone marrow (BM).

The MSCs for use according to the present invention may originate from various tissues or body fluids, in particular from blood, BM, fat tissue or amniotic tissue. Bone marrow harvesting of MSCs has been reportedly associated with haemorrhage, chronic pain, neurovascular injury, and even death. Adipose tissue as a source for MSCs is regarded as a safer option. However, harvesting of MSCs from adipose tissue still requires an incision in the donor animal, hence this is still an invasive procedure. MSCs derived from blood show similar morphology as MSCs derived from bone marrow and adipose tissue. As a consequence, by preference, the MSCs originate from blood, including but not limited to umbilical cord blood and peripheral blood. More preferably, the MSCs originate from peripheral blood. Blood is not only a non-invasive and painless source, but also simple and safe to collect and, consequently, easily accessible and prone to less complications afterwards. The MSCs or blood comprising MSCs may originate from all mammals, including, but not limited to, humans, domestic and farm animals, zoo animals, sport animals, pet animals, companion animals and experimental animals, such as, for example, mice, rats, rabbits, dogs, cats, cows, horses, pigs and primates, e.g., monkeys and apes; especially horse, human, cat, dogs, rodents, etc. In an embodiment, said origin of is equine. In particular MSCs may be derived from peripheral blood, preferably equine peripheral blood, which allows multiple MSC collections per year with minimal discomfort or morbidities for the donor animal.

In some cases, the use of allogeneic or xenogeneic MSCs is a more favorable option as they offer a stringent selection of healthy and high-quality stem cell donors. They allow the production of a ready-to-use product, avoiding the invasive harvesting and time-consuming cultivation of MSCs from each individual patient. Because of the relative low culture capacity of canine and feline MSCs compared to for example equine or human MSCs, the use of xenogeneic (e.g. human or equine) MSCs is preferred above allogeneic canine and feline MSCs, especially for commercial applications, such as for use in the treatment of AD in canines and felines.

Therefore, in a particular embodiment the MSCs of the current invention may be used for allogeneic or xenogeneic administration to a subject. As already indicated, allogeneic or xenogeneic use allows a better control of the quality of the MSCs, as different donors may be screened, and the optimal donors may be selected. The latter is indispensable in view of preparing functional MSCs. This is in contrast to autologous use of MSCs, as in this case, quality of the cells is more difficult to be ensured. Nonetheless, autologous use may have his benefits as well. In one case, blood MSCs are isolated, for which blood from a donor was used who was later also recipient of the isolated MSCs. In another case, blood is used from donors in which the donor is preferably of the same family, gender or race as the recipient of the MSCs isolated from the blood of donors. In particular, these donors will be tested on common current transmittable diseases or pathologies, in order to avoid the risk of horizontal transmission of these pathologies or diseases through the stem cells. Preferably, the donors/donor animals are kept in quarantine. When using donor horses they can be, for example tested for the following pathologies, viruses or parasites: equine infectious anemia (EIA), equine rhinopneumonitis (EHV-1, EHV-4), equine viral arteritis (EVA), West Nile virus (WNV), African horse Sickness (AHS), dourine (*Trypanosoma*), equine piroplasmosis, glanders (malleus, glanders), equine influenza, Lyme borreliosis (LB) (*Borrelia burgdorferi*, Lyme disease).

In an embodiment, the MSCs for use of the present invention may be characterized by the presence of/are measured positive for one or more of the following markers CD29, CD44, CD90, CD105, vimentin, fibronectin, Ki67, CK18 or any combination thereof. In a further embodiment, the MSCs for use of current invention may be characterized by the presence of mesenchymal markers CD29, CD44 and CD90. By means of the latter, the purity of the obtained MSCs can be analyzed, and the percentage of MSCs can be determined.

CD29 is a cell surface receptor encoded by the integrin beta 1 gene, wherein the receptor forms complexes with other proteins to regulating physiological activities upon binding of ligands. The CD44 antigen is a cell surface glycoprotein involved in cell-cell interactions, cell adhesion and migration. In addition, is CD44 a receptor for hyaluronic acid and can also interact with other ligands such as osteopontin, collagens and matrix metalloproteinases (MMPs). The CD90 antigen is a conserved cell surface protein considered as a marker for stem cells, like MSCs. The MSCs of current invention being triple positive for CD29/CD44/CD90 enables the person skilled in the art for a fast and unambiguous selection of the MSCs and provides the MSCs biological properties which are of interest for further downstream applications.

In an embodiment, the MSCs for use of the current invention are characterized by the absence of/measure negative for Major Histocompatibility Complex (MHC) class II molecules, preferably all currently known MHC Class II molecules, classifying the cell as a cell that can be used in cellular therapy for mammalians, such as canine or feline cellular therapy. Even when the MSCs are partly differentiated, the MSCs remain negative for MHC class II molecules. Detecting presence or absence, and quantifying the expression of MHC II molecules can be performed using flow cytometry.

In another and further embodiment the MSCs measure negative for CD45 antigen, a marker for hematopoietic cells.

In an embodiment, the MSCs measure negative for both MHC class II molecules and CD45.

In a particularly preferred embodiment, the MSCs for use of the current invention measure positive for mesenchymal markers CD29, CD44 and CD90 and measure negative for MHC class II molecules and CD45.

MSCs in general express MHC Class I antigen on their surface. In a particular embodiment the MSCs for use of current invention have a low or undetectable level of the MHC Class I marker. In a most preferred embodiment said MSCs measure negative for MHC Class II markers and have a low or undetectable level of MHC Class I marker, wherein said cell exhibits an extremely low immunogenic phenotype. For the sake of the current invention, said low level should be understood as less than 25%, more preferably less than 15% of the total cells expressing said MHC I or MHC II. Detecting presence or absence, and quantifying the expression of MHC I and MHC II molecules can be performed using flow cytometry.

These immunological properties of the MSCs limit the ability of the recipient immune system to recognize and reject cells, preferably allogeneic or xenogeneic cells, following cellular transplantation. The production of factors by MSCs, that modulate the immune response together with their ability to differentiate into appropriate cell types under local stimuli make them desirable stem cells for cellular therapy.

In an embodiment, the MSCs for use of the invention, secrete immunomodulatory prostaglandin E2 cytokine when present in an inflammatory environment or condition.

Inflammatory environments or conditions are characterized by the recruitment of immune cells of the blood. Inflammatory mediators include prostaglandins, inflammatory cytokines such as IL-1B, TNF-α, IL-6 and IL-15, chemokines such as IL-8 and other inflammatory proteins like TNF-α, IFN-γ. These mediators are primarily produced by monocytes, macrophages, T-cells, B-cells to recruit leukocytes at the site of inflammation and subsequently stimulate a complex network of stimulatory and inhibitory interactions to simultaneously destruct and heal the tissue from the inflammatory process.

Prostaglandin E2 (PgE2) is a subtype of the prostaglandin family. PgE2 is synthesized from arachidonic acid (AA) released from membrane phospholipids through sequential enzymatic reactions. Cyclooxygenase-2 (COX-2), known as prostaglandin-endoperoxidase synthase, converts AA to prostaglandin H2 (PgH2), and PgE2 synthase isomerizes PgH2 to PgE2. As a rate-limiting enzyme, COX-2 controls PgE2 synthesis in response to physiological conditions, including stimulation by growth factors, inflammatory cytokines and tumor promoters.

In a particular embodiment, said MSCs present in an inflammatory environment secrete the soluble immune factor prostaglandin E2 (PgE2) in a concentration ranging between $10^3$ to $10^6$ picogram per ml to induce or stimulate MSC-regulated immunosuppression.

The PgE2 secretion of the MSCs in those specific concentration ranges stimulates anti-inflammatory processes in vitro and together with their ability to differentiate into appropriate cell types makes them desirable for cellular transplantation.

In a preferred embodiment the MSCs for use of the current invention measures:
- positive for mesenchymal markers CD29, CD44 and CD90;
- positive for one or more markers comprised in the group consisting of vimentin, fibronectin, Ki67, or a combination thereof;
- negative for MHC class II molecules;
- negative for hematopoietic marker CD45; and
- preferably have a low or undetectable level of MHC Class I molecules, wherein said low level should be understood as less than 25%, more preferably less than 15% of the total cells expressing MHC I.

In a most preferred embodiment, the MSCs for use of the current invention measures: positive for mesenchymal markers CD29, CD44 and CD90;
- positive for one or more markers comprised in the group consisting of vimentin, fibronectin, Ki67, or a combination thereof;
- negative for MHC class II molecules;
- negative for hematopoietic marker CD45; and
- preferably have a low or undetectable level of MHC Class I molecules, wherein said low level should be understood as less than 25%, more preferably less than 15% of the total cells expressing MHC I, wherein said cell secretes immunomodulatory PgE2 cytokine in a concentration ranging between $10^3$ to $10^6$ picogram per ml when present in an inflammatory environment or condition.

In another or further embodiment, the MSCs for use according to the invention, have an increased secretion of at least one of the molecules chosen from IL-6, IL-10, TGF-beta, NO or a combination thereof, and a decreased secretion of IL-1 when present in an inflammatory environment or condition, and compared to an MSC having the same characteristics but not being subjected to said inflammatory environment or condition.

In a preferred embodiment, the MSCs have an increased secretion of at least one of the molecules chosen of IL-6, IL-10, TGF-β, NO, or a combination thereof, and a decreased secretion of IL-1 when present in an inflammatory environment or condition. Comparison can be made with a mesenchymal stem cell having the same characteristics as presented above, but which is not subjected to said inflammatory environment or condition.

Preferably the MSCs have an increased secretion of PgE2 in combination with two or more of the abovementioned factors.

PgE2, IL-6, IL-10, TGF-B and NO help suppressing the proliferation and function of major immune cell populations like T cells and B cells. In addition, the MSCs express low levels of MHC class I molecules and/or are negative for MHC class II molecules on their surface, escaping immunogenic reactions. In addition, the MSCs of current can suppress the proliferation of white blood cells by their increased secretion of abovementioned factors, once again helping to avoid immunogenic reactions of the host.

In another or further embodiment the MSCs stimulate the secretion of PgE2, IL-6, IL-10, NO, or a combination thereof and/or suppress the secretion of TNF-α, IFN-γ, IL-1, IL-13, or a combination thereof in the presence of peripheral blood mononuclear cells (PBMCs). In another or further embodiment, the MSCs suppress the secretion of TGF-β1 in the presence of PBMCs.

In the inflammatory environment the MSCs secrete multiple factors that modulate the immune response of the host. In addition, the MSCs have the stimulatory effect to induce or stimulate the secretion of one or more factors selected from the group consisting of PgE2, IL-6, IL-10, NO, or a combination thereof. Next to the stimulatory effect of the MSCs on the PBMCs in an inflammatory environment, the MSCs also have an suppressive effect on the secretion of the PBMCs, resulting in a decrease of one or more factors selected from the group consisting of TNF-α, IFN-γ, IL-1, TGF-β1, IL-13, or a combination thereof. The MSCs have a regulatory effect in the inflammatory environment, making them useful in the treatment of all sorts of diseases, particularly disorders of the immune system.

In general, any technology for identifying and characterizing cellular markers for a specific cell type (e.g. mesenchymal, hepatic, hematopoietic, epithelial, endothelial markers) or having a specific localization (e.g. intracellular, on cell surface, or secreted) that are published in the literature may be considered appropriate for characterizing MSCs. Such technologies may be grouped in two categories: those that allow maintaining cell integrity during the analysis, and those based on extracts (comprising proteins, nucleic acids, membranes, etc.) that are generated using such cells. Among the technologies for identifying such markers and measuring them as being positive or negative, immunocytochemistry or analysis of cell culture media are preferred since these allow marker detection even with the low amount of cells, without destroying them (as it would be in the case of Western Blot or Flow Cytometry).

Immunomodulatory properties of MSCs may be assayed using an MLR assay. For this MLR assay responder T-cells are marked with a fluorescent dye which lights up green when it is exposed to a specific light frequency. These responder T-cells are then stimulated with a plant mitogen (ConA) to induce or stimulate proliferation. When the T-cells start to divide the dye is distributed over their daughter cells, so the dye is serially diluting with every cell division. Therefore, the amount of proliferation of T-cells can be measured by looking at the decrease of color. Thus, to investigate the immunomodulatory properties of the MSCs, these MSCs are added to the stimulated responder T-cells and co-incubated for several days. Appropriate positive and negative controls are included to see if the test is performed successfully. At the end of the incubation period, the amount of T-cell proliferation is measured using flow cytometry, enabling us to see whether or not the MSCs suppressed the T-cell proliferation.

Relevant biological features of the MSCs can be identified by using technologies such as flow cytometry, immunocytochemistry, mass spectrometry, gel electrophoresis, an immunoassay (e.g. immunoblot, Western blot, immunoprecipitation, ELISA), nucleic acid amplification (e.g. real time RT-PCR), enzymatic activity, omics-technologies (proteomics, lipidomics, glycomics, translatomics, transcriptomics, metabolomics) and/or other biological activity.

The MSCs of current invention may be derived by any standard protocol known in the art. In an embodiment, said MSCs may be obtained via a method wherein the MSCs are isolated from blood or a blood phase and wherein said cells are cultured and expanded in a basal medium, preferably a low glucose medium.

Basal medium formulation as known in the art include, but are not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Liebovitz L-15, DMEM/F-12, Essential Modified Eagle's Medium (EMEM), RPMI-1640, Medium 199, Waymouth's 10 MB 752/1 or Williams Medium E, and modifications and/or combinations thereof. Compositions of the above basal media are generally known in the art and it is within the skill of one in the art to modify or modulate concentrations of media and/or media supplements as necessary for the cells cultured. A preferred basal medium formulation may be one of those available commercially such as DMEM, which are reported to sustain in vitro culture of MSCs, and including a mixture of growth factors for their appropriate growth, proliferation, maintenance of desired markers and/or biological activity, or long-term storage.

Such basal media formulations contain ingredients necessary for mammal cell development, which are known per se. By means of illustration and not limitation, these ingredients may include inorganic salts (in particular salts containing Na, K, Mg, Ca, CI, P and possibly Cu, Fe, Se and Zn), physiological buffers (e.g., HEPES, bicarbonate), nucleotides, nucleosides and/or nucleic acid bases, ribose, deoxyribose, amino acids, vitamins, antioxidants (e.g., glutathione) and sources of carbon (e.g. glucose, pyruvate, e.g., sodium pyruvate, acetate, e.g., sodium acetate), etc. It will also be apparent that many media are available as low-glucose formulations with or without sodium pyruvate.

Method for isolating MSCs from blood or a blood phase and culturing and expanding said cells are known in the art and for instance described in WO2014053418 or WO2014053420.

In an embodiment, such method for isolating MSCs from blood or a blood phase and culturing and expanding said cells in a low glucose medium may comprise the following steps:
a) the collection of one or more blood samples from donors, in a sample vial, coated with an anti-coagulant;
b) centrifuging the blood samples to obtain a 3-phase distribution, consisting of a plasma-phase, buffy coat, and erythrocytes phase;
c) collecting the buffy coat and loading it on a density gradient;
d) collecting of the blood-inter-phase obtained from the density gradient of step c);
e) isolating of MSCs from the blood-inter-phase by centrifugation;
f) seeding between $2.5\times10^5/cm^2$ and $5\times10^5/cm^2$ MSCs in culture and keeping them in a low glucose growth medium supplemented with dexamethasone, antibiotics and serum.

In an embodiment, anticoagulants may be supplemented to the MSCs. Non-limiting examples are EDTA or heparin.

The number of seeding is crucial to ultimately obtain a pure and viable population MSCs at an acceptable concentration, as a too dense seeding will lead to massive cell death during expansion and a non-homogenous population of MSCs and a too dispersed seeding will result in little or no colony formation of MSCs, so that expansion is not or hardly possible, or it will take too much time. In both cases the viability of the cells will be negatively influenced.

In a preferred embodiment of current invention, the MSCs have a high cell viability, wherein at least 90%, more preferably at least 95%, most preferably 100% of said cells are viable.

The blood-interphase is the source of blood mononuclear cells (BMCs) comprising monocytes, lymphocytes, and MSCs. By preference, the lymphocytes are washed away at 37° C., while the monocytes die within 2 weeks in the absence of cytokines necessary to keep them alive. In this way, the MSCs are purified. The isolation of the MSCs from the blood-inter-phase is preferably done by means of centrifugation of the blood-inter-phase, after which the cell pellet is washed at least once with a suitable buffer, such as a phosphate buffer.

In a further embodiment the MSCs of current invention are negative for monocytes and macrophages, both within a range between 0% and 7.5%.

In particular, the mesenchymal cells are kept at least 2 weeks in growth medium. Preferably, growth medium with 1% dexamethasone is used, as the specific characteristics of the MSCs are kept in said medium.

Following a minimum period of 2 weeks (14 days), preferably 3 weeks (21 days) MSC colonies will become visible in the culture bottles. In a subsequent step g) at least $6\times10^3$ stem cells/cm$^2$ are transferred to an expansion medium containing low glucose, serum and antibiotics for the purpose of expanding the MSCs. Preferably, the expansion of the MSCs will occur in minimal five cell passages. In this way sufficient cells can be obtained. Preferably, the cells are split at 70% to 80% confluency. The MSCs can be maintained up to 50 passages in culture. After this the risk of loss in vitality, senescence or mutation formation occurs.

In a further embodiment, the population doubling time (PDT) between each passage during expansion of the MSCs should be between 0.7 and 3 days after trypsinization. Said PDT between each passage during expansion of the MSCs is preferably between 0.7 and 2.5 days after trypsinization.

In a preferred embodiment, the MSCs for use according to the invention have a spindle-shaped morphology. The morphological characterization of the MSCs of current invention classifies the cell as an elongated, fibroblast-like, spindle-shaped cell. This type of cell is distinct form other populations of MSCs with small self-renewing cells which reveal mostly a triangular or star-like cell shape and populations of MSCs with a large, cuboidal or flattened pattern with a prominent nucleus. The selection of MSCs with this specific morphological characteristic along with the biological markers enables the person skilled in the art to isolate the MSCs of current invention. A morphological analysis of cells can easily be performed by a person skilled in the art using phasecontrast microscopy. Besides, the size and granularity of MSCs can be evaluated using forward and side scatter diagram in flow cytometry or other techniques known by a person skilled in the art.

In another or further preferred embodiment, the MSCs have a suspension diameter between 10 μm and 100 μm. The MSCs for use of current invention have been selected based on size/suspension diameter. By preference, the MSCs have a cell size between 10 to 100 μm, more preferably between 15 and 80 μm, more preferably 20 and 75 μm, more preferably between 25 and 50 μm. Preferably, the selection of cells based on cell size occurs by a filtration step. For instance, MSCs with a cell concentration ranging between $10^3$ to $10^7$ MSCs per ml, wherein said cells are preferably diluted in low glucose DMEM medium, are selected by size by means of a filter system, wherein the cells are run through a double filtration step using a 40 μm filter. Double or multiple filtration steps are preferred. The latter provides for a high population of single cells and avoids the presence of cell aggregates. Such cell aggregates may cause cell death during the preservation of the cells by freezing and may all have an impact on further downstream applications of the cells. For instance, cell aggregates may higher the risk of the occurrence of a capillary embolism when administered intravenously.

In an embodiment, said therapeutically effective amount of MSCs is between $10^5$-$10^7$ MSCs in said composition.

In a preferred embodiment, the MSCs for use according to the present invention are formulated for administration in a subject by means of intravenous injection or infusion.

In an embodiment, with each intravenous injection or infusion, a therapeutically effective amount of MSCs is administered, preferably each injection or infusion comprises a dose of $10^5$ to $10^7$ of said MSCs. Preferably, the MSCs are administered through intravenous injection.

In an embodiment, a therapeutically effective amount of MSCs is administered to the canine or feline patient, preferably a dose of $10^5$-$10^7$ MSCs, more preferably a dose of $10^5$-$10^6$ MSCs per patient is administered. In an embodiment, a single dose is administered.

The minimum therapeutically effective dose that yields a therapeutic benefit to a subject is at least $10^5$ of the MSCs per administration. Preferably, each administration is by intravenous injection and comprises between $10^5$ to $5\times10^5$ MSCs per administration, wherein said MSCs preferably are native and/or xenogeneic.

In an embodiment, said MSCs are administered at least twice, at least three times, at least four times, at least five times, preferably with intervals.

In another or further embodiment, the treatment further comprises: multiple administrations of the MSCs or the composition comprising MSCs, for example multiple intravenous administrations, doses of $10^5$-$10^7$ MSCs per canine or feline patient, wherein said multiple doses are administered at various time points, including but not limited to one or more of the following time points 1 day apart, 2 days apart, 3 days apart, 4 days apart, 5 days apart, 6 days apart, 7 days (1 week) apart, 2 weeks apart, 3 weeks apart, 4 weeks apart, 5 weeks apart, 6 weeks apart, 7 weeks apart, 8 weeks apart, 3 months apart, 6 months, 9 months apart, and/or 1 year apart. Preferably each dose is administered at least 2 weeks apart, more preferably at least 3 weeks apart, even more preferably at least 4 weeks apart, and most preferably at least 6 weeks apart.

In an embodiment, said composition comprises said MSCs present in a sterile liquid. A non-limiting example of such sterile liquid is a minimal essential medium (MEM), such as Dulbecco's Modified Eagle Medium (DMEM). Said sterile liquid should be safe for intravenous administration, e.g. via injection or infusion, to a mammalian patient.

As non-limiting examples, said sterile liquid is a minimal essential medium, such as a basal medium. Basal medium formulation as known in the art include, but are not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Liebovitz L-15, DMEM/F-12, Essential Modified Eagle's Medium (EMEM), RPMI-1640, Medium 199, Waymouth's 10 MB 752/1 or Williams Medium E, and modifications and/or combinations thereof. Compositions of the above basal media are generally known in the art and it is within the skill of one in the art to modify or modulate concentrations of media and/or media supplements as necessary for the cells cultured. A preferred basal medium formulation may be one of those available commercially such as DMEM, which are reported to sustain in vitro culture of MSCs, and including a mixture of growth factors for their appropriate growth, proliferation, maintenance of desired markers and/or biological activity, or long-term storage.

Such basal media formulations contain ingredients necessary for mammal cell development, which are known per se. By means of illustration and not limitation, these ingredients may include inorganic salts (in particular salts containing Na, K, Mg, Ca, Cl, P and possibly Cu, Fe, Se and Zn), physiological buffers (e.g., HEPES, bicarbonate), nucleotides, nucleosides and/or nucleic acid bases, ribose, deoxyribose, amino acids, vitamins, antioxidants (e.g., glutathione) and sources of carbon (e.g. glucose, pyruvate, e.g., sodium pyruvate, acetate, e.g., sodium acetate), etc. It will also be apparent that many media are available as low-glucose formulations with or without sodium pyruvate.

By preference, said composition comprises at least 75%, more preferably at least 80%, even more preferably at least 85%, most preferably at least 90% of single cells and whereby said single cells have a suspension diameter of between 10 μm and 100 μm, more preferably between 15 μm and 80 μm, more preferably between 20 μm and 75 μm, more preferably between 25 μm and 50 μm. As previously mentioned, the diameter of the cells as well as their single-cell nature is crucial for any downstream application, e.g. intravenous administration, and for the vitality of the cells.

By preference, said composition comprises at least 90% MSCs, more preferably it will comprise at least 95% MSCs, more preferably at least 99%, most preferably 100% MSCs.

The volume and concentration of the composition in the form of a sterile liquid comprising the MSCs is preferably adapted for intravenous injection. In an embodiment, the pharmaceutical composition may be administered to the animal in the form of a sterile liquid comprising, after final adjustment, the MSCs at a concentration of $10^5$-$10^7$ cells per mL.

In an embodiment, with each intravenous injection or infusion, a therapeutically effective amount of MSCs is administered, preferably each injection or infusion comprises a dose of $10^5$ to $10^7$ of said MSCs.

In an embodiment, the pharmaceutical composition comprises a therapeutically effective of amount of MSCs of between $10^5$-$10^7$ MSCs per mL, preferably $10^5$ to $10^6$ MSCs per mL, more preferably $10^5$-$5\times10^5$ MSCs per mL of said composition.

In an embodiment, one dosage of said composition has a volume of about 0.5 to 5 ml, preferably of about 0.5 to 5 ml, preferably of about 0.5 to 3 ml, preferably of about 0.5 to 2 ml, more preferably of about 0.5 to 1.5 ml, most preferably of about 1 ml. In another or further embodiment, one dosage of said composition has a volume of maximally about 5 ml, preferably maximally about 4 ml, more preferably maximally about 3 ml, more preferably maximally about 2 ml, most preferably said volume is about 1 ml. This amount is suitable for intravenous administration.

Said dosage may be formulated in a vial or in a pre-filled syringe.

In an embodiment, the composition further comprises components selected from the group consisting of platelet-rich plasma (PRP), hyaluronic acid, compositions based on hyaluronic acid, glycosaminoglycans, or compositions based on glycosaminoglycans, or any combination thereof. These are known to have additional beneficial functions during downstream applications of the composition according to the current invention. Mixing of the MSCs with such carrier substances may in some cases be desirable to increase the effectiveness of the composition or create a synergistic effect. For instance, said carrier substances aid in the homing capacities and immunomodulating effects of the MSCs in the cell composition. PRP, for example, a substance rich in growth factors, stimulate the stem cells after implantation. Preferably, both the stem cells and PRP are harvested from the same donors for compatibility reasons. Carrier substances can also be used to counteract gravity: stem cells follow the law of gravity and therefore have difficulties reaching higher lesions without a carrier in which they can migrate. In addition, the carrier substances themselves also have beneficial effects on the pathological environment in which they contribute to the tissue repair itself and also provide a good stem cell niche to help differentiation of the cells in this area. Examples of hyaluronic acid, glycosaminoglycans or compositions on this basis include OSTENIL®, OSTENIL®$^+$, Adant® and Adequan®.

In an embodiment, the volume of the composition which is administered per injection to a patient is adapted in accordance with the patient's body weight. In another embodiment, a fixed dose of $10^5$-$10^7$ MSCs per patient, preferably $10^5$ to $10^6$ MSCs, more preferably $10^5$-$5\times10^5$ MSCs, most preferably $3\times10^5$ MSCs is administered.

The inventors have further discovered that a particularly effective treatment is achieved by a dosing regimen comprising at least two dosages of the MSCs for use or the pharmaceutical composition for use as described above in any of the embodiments.

Therefore, a further embodiment relates to a pharmaceutical composition for use in the treatment of atopic dermatitis in canines and felines, wherein:

the treatment comprises a step of administering, preferably intravenously, a first amount of said composition comprising a total dose of $10^5$-$10^7$ MSCs per patient, and the treatment further comprises a step of administering, preferably intravenously, a second amount of said composition, said second amount comprising a second total dose of $10^5$-$10^7$ MSCs, wherein said MSCs preferably are native and/or xenogeneic, and wherein said second dose is administered 1 day after the first amount, 2 days after the first amount, 3 days after the first amount, 4 days after the first amount, 5 days after the first amount, 6 days after the first amount, 7 days (1 week) after the first amount, 2 weeks after the first amount, 3 weeks after the first amount, 4 weeks after the first amount, 5 weeks after the first amount, 6 weeks after the first amount, 7 weeks after the first amount, 8 weeks after the first amount, 3 months after the first amount, 6 months, 9 months after the first amount, and/or 1 year after the first amount. Preferably each dose is administered at least 2 weeks after the first amount, more preferably at least 3 weeks after the first amount, even more preferably at least 4 weeks after the first amount, and most preferably at least 6 weeks after the first amount.

In an embodiment, said second dose is identical to the first dose. In another embodiment, said second dose is lower than the first dose. In yet another embodiment, said second dose is higher than the first dose.

In an embodiment, a third, fourth and/or even a fifth amount of said composition may be administered, preferably intravenously, to said patient, wherein said third, fourth and/or fifth amount comprises a third, fourth and/or fifth total dose of $10^5$-$10^7$ MSCs, wherein said MSCs preferably are native and/or xenogeneic.

In an embodiment, a sixth or more amount of said composition may be administered, preferably intravenously, to said patient, wherein said sixth or more amount comprises a sixth or more total dose of $10^5$-$10^7$ MSCs, wherein said MSCs preferably are native and/or xenogeneic.

In an embodiment, the present invention relates to MSCs or a pharmaceutical composition comprising a therapeutically effective amount of MSCs for use in the treatment of AD-associated clinical and/or histopathological symptoms in canines or felines diagnosed with or suffering from atopic dermatitis. The MSCs are as described in any of the embodiments above.

As indicated before, typical clinical symptoms of atopic dermatitis in canines and felines, such as domestic dogs or cats, may include pruritus (itching) and various skin lesions.

The most common clinical sign of AD and reason for presentation is pruritus, which may be nonseasonal, seasonal, or nonseasonal with seasonal worsening. The severity degree of pruritus can be evaluated using a scoring scheme, for example a Pruritis Visual Analog Scale (pVAS) scoring scheme. The pVAS is a scale consisting of a 10 cm long line and a single question. It is most commonly used in clinical trials for measuring itch intensity and features high reliability and concurrent validity.

In dogs this scoring system can be based on the article of Rybníček et al., 2019 (doi.org/10.1111/j.1365-3164.2008.00728.x). In this scoring system, the left end point represents "no itch" and the right end point the "extreme itch". It can be interpreted as follows: VAS 0="normal (itching is not a problem), VAS 2="very mild pruritus/only occasional episodes", VAS 4="mild pruritus (not when sleeping, eating, playing, exercising or being distracted", VAS 6="moderate pruritis/regular episodes (itching might occur at night, but not when eating, playing, exercising or being distracted)", VAS 8="severe pruritus/prolonged episodes", VAS 10="extremely severe pruritus (needs to be physically restrained from itching)".

In cats an adapted dual feline pVAS scoring scheme can be used (see Table 1). Both the licking and scratching behavior of the cat is scored on a scale from 0 to 10 in this scheme.

TABLE 1

Dual feline pruritus Visual Analog Scale.
Pruritus prompts cats to groom excessively and/or scratch using the hind limbs. A healthy cat, free from pruritus, spends about 1 h per day grooming (normal grooming behavior) and scratches around 1 min. per day. Please read carefully (from the bottom to the top) the behavioral descriptors on the right and left side and mark on both lines how much your cat licks/scratches, on average, over 24 h.

| How much LICKING? | How much SCRATCHING? |
|---|---|
| Nonstop or nearly nonstop licking My cat over-grooms even during the visit and/ or hides constantly. Licking results invariably in hair loss and often includes skin lesions. | Nonstop or nearly nonstop scratching My cat scratches even during the visit and/ or hides constantly. Scratching results invariably in skin lesions. |
| Intense and prolonged licking My cat wakes up and/or stops eating/playing to licking, and/or hides very often. Licking induces hair loss very frequently. | Intense and prolonged scratching My cat wakes up and/or stops eating/playing to scratching, and/or hides very often. Scratching results in skin lesions very frequently. |
| Moderate licking My cat often hides and wakes up sometimes to grooming but never stops eating or playing to do so. Licking often results in hair loss. | Moderate scratching My cat often hides and wakes up sometimes to scratching but never stops eating or playing to do so. Scratching often results in skin lesions. |
| Frequent and protracted mild licking My cat never grooms while eating, sleeping or playing. It occasionally hides. Licking seldom results in hair loss. | Frequent and protracted mild scratching My cat never scratches while eating, sleeping or playing. It occasionally hides. Scratching seldom results in skin lesions. |
| Mild and episodic licking My cat grooms more than it used to. Licking never results in hair loss. | Mild and episodic scratching My cat scratches more than it used to. Scratching never results in skin lesions. |
| Healthy cat: licking up to 1 h a day | Healthy cat: scratching up to 1 min. a day |

In an embodiment, the MSCs or the pharmaceutical composition comprising MSCs are used for treating a canine or a feline with a pVAS score of at least 1 prior to administration of the MSCs or the pharmaceutical composition comprising MSCs and the pVAS score has a relative decrease of at least 20% within a period of 1 month after one or more administrations of the MSCs or the pharmaceutical composition comprising MSCs in at least 35% of the canines or felines treated with the MSCs or the pharmaceutical composition comprising MSCs.

Another clinical symptom in AD are skin lesions. The severity of these skin lesions can be evaluated using a skin lesion scoring scheme. In dogs this scoring scheme can be for instance a Canine Atopic Dermatitis Extent and Severity Index (CADESI)-04 scoring scheme. In this scheme a score is provided for three different lesions (erythema, lichenification and alopecia/excoriation) from 0 to 3 at 20 body sites typically affected in atopic dogs. Benchmarks for mild, moderate and severe AD skin lesions are 10, 35 and 60, respectively.

Two systems of evaluation are used to clinically assess the severity of lesions in felines: Scoring Feline Allergic Dermatitis (SCORFAD) and the Feline Extent and Severity Index (FeDESI). The SCORFAD system assesses the severity and extent of 4 types of lesions on a scale of 0 to 4: abrasions, eosinophilic plaques, miliary dermatitis, and pruritic alopecia. SCORFAD has been partially validated and is recommended for use in assessing the severity of allergic skin diseases in cats. The FeDESI system is an adaptation of the Canine Atopic Dermatitis Extent and Severity Index (CADESI), which is used in dogs. It evaluates erythema, excoriations/erosions, and self-induced alopecia in 42 body areas on a scale of 0 to 5, with a cat obtaining a maximum of 630 points and is described in the article from Steffan J et al. (DOI: 10.1111/j.1365-3164.2012.01071.x).

As canines and felines suffering from AD often present with multiple skin lesions, intravenously administering MSCs or a pharmaceutical composition comprising MSCs offers substantial benefits in therapy in multiple locations at once, compared to local subcutaneous administration of MSCs.

In an embodiment, the canines suffering from AD have a CADESI-04 score of at least 10 prior to administration of the MSCs or the pharmaceutical composition comprising MSCs and, after one or more administrations of the MSCs or the pharmaceutical composition comprising MSCs, said CADESI-04 score has a relative decrease of at least 25%, more preferably 30%, in at least 35% of the canines treated with the MSCs or the pharmaceutical composition comprising MSCs within a period of 1 month.

In an embodiment, the felines suffering from AD have a SCORFAD score or a FeDESI score of at least 10 prior to administration of the MSCs or the pharmaceutical composition comprising MSCs and, after one or more administrations of the MSCs or the pharmaceutical composition comprising MSCs, said score has a relative decrease of at least 25%, more preferably 30%, in at least 35% of the felines treated with the MSCs or the pharmaceutical composition comprising MSCs within a period of 1 month.

When looking more at the histopathological symptoms of AD in canines and felines, the histopathology of canine AD lesional skin is similar to human AD lesional skin. The epidermis shows mild to severe hyperplasia and mild, to sometimes patchy spongiosis. Exocytosis of lymphocytes into the epidermis is present. In the dermis, superficial perivascular dermatitis with infiltration of a mix of T-lymphocytes and dendritic antigen-presenting cells is seen.

In an embodiment, the MSCs or the pharmaceutical composition comprising MSCs is used in the treatment of lymphocytic perivascular dermatitis with infiltrating T cells in skin lesions of canines or felines diagnosed with or suffering from atopic dermatitis.

After cutaneous allergen exposure, antigen-presenting cells (APC) in the skin can take up and process allergens. They activate naïve T cells in regional lymph nodes through presentation of allergenic peptides by MHC molecules on their surfaces. Specific recognition of the allergen-MHC-complex by the T cell receptor (TCR) combined with concurrent co-stimulatory signals leads to activation, proliferation and differentiation of naïve T cells, followed by T cell skin homing. This results in accumulation of allergen-specific T cells at the affected sites in the skin. The infiltrating cutaneous T cells consist of both $CD4^+$ and $CD8^+$ subsets with a predominance of dermal $CD4^+$ T cells, which can be subdivided in different populations, such as T-helper 1 and T-helper 2 T cells, based on phenotype and function.

In an embodiment, said skin lesions of said canine or feline diagnosed with or suffering from atopic dermatitis demonstrate a decreased number of infiltrating $CD4^+$ T cells after one or more administrations of the MSCs or the pharmaceutical composition comprising MSCs, wherein said decrease comprises at least 15% of the number of infiltrating $CD4^+$ T cells present prior to administration of the MSCs or the pharmaceutical composition comprising MSCs in said canine or feline. In an embodiment, both the number of infiltrating Th1 and Th2 cells is reduced after administration of said MSCs or the pharmaceutical composition comprising MSCs. In an embodiment, this decrease in Th1 and Th2 cells is reflected by a decreased secretion of the cytokines IFN-γ, IL-4 and/or IL-13.

In an embodiment, the present invention relates to MSCs or a pharmaceutical composition comprising MSCs for use as a prophylactic treatment in canines and felines diagnosed with or suffering from atopic dermatitis. In an embodiment, the MSCs or the pharmaceutical composition comprising a therapeutically effective amount of MSCs is used in the prevention of one or more symptoms associated with AD exacerbations. In an embodiment, said symptom comprises pruritus. In another embodiment, said symptom comprises atopic dermatitis-associated skin lesions. In another embodiment, said symptom comprises lymphocytic perivascular dermatitis with infiltrating T cells. In an embodiment, the MSCs or the pharmaceutical composition comprising MSCs are used as a prophylactic treatment in the prevention of two or more of the aforementioned symptoms associated with AD exacerbations in canines and felines diagnosed with or suffering from atopic dermatitis.

When a disbalanced immune system contributes to disease, immunomodulatory agents may be used to help driving the immune system back into the right direction.

In a second aspect, the present invention relates to MSCs or a pharmaceutical composition comprising a therapeutically effective amount of MSCs for use as an immunomodulating agent during the acute and/or the chronic phase of the AD inflammatory reaction in canines and felines diagnosed with or suffering from atopic dermatitis.

In an embodiment, administration of said immunomodulating agent decreases the lymphocytic perivascular dermatitis in skin lesions in canines and felines diagnosed with or suffering from atopic dermatitis by reducing the number of infiltrating $CD4^+$ T cells with 15% in comparison with the number of infiltrating $CD4^+$ T cells prior to administration.

In an embodiment, both the number of infiltrating Th1 and Th2 cells, which are two different $CD4^+$ T helper subsets, is reduced after administration of said immunomodulating agent. In an embodiment, this decrease in Th1 and Th2 cells is reflected by a decreased secretion of the cytokines IFN-γ and/or IL-13 and IL-4.

In a last aspect, the present invention relates to a specific pharmaceutical composition comprising peripheral blood-derived MSCs. Said composition comprises native peripheral blood-derived MSCs, said MSCs are animal-derived, preferably mammal-derived, and present in a sterile liquid at a concentration of between $10^5$-$10^7$ MSCs per mL of said composition, wherein one dosage of said composition has a volume of about 0.5 to 5 ml, wherein said MSCs measure positive for mesenchymal markers CD29, CD44 and CD90 and measure negative for MHC class II molecules and CD45, and wherein said MSCs have a suspension diameter between 10 μm and 100 μm.

In an embodiment, said pharmaceutical composition is intravenously administered. In a preferred embodiment, said MSCs are equine derived.

In an embodiment, said one dosage of said composition has a volume of about 0.5 to 5 ml, preferably of about 0.5 to 5 ml, preferably of about 0.5 to 3 ml, preferably of about 0.5 to 2 ml, more preferably of about 0.5 to 1.5 ml, most preferably of about 1 ml. In another or further embodiment, one dosage of said composition has a volume of maximally about 5 ml, preferably maximally about 4 ml, more preferably maximally about 3 ml, more preferably maximally about 2 ml, most preferably said volume is about 1 ml. This amount is suitable for intravenous administration.

In another or further preferred embodiment, the MSCs have a suspension diameter between 15 and 80 μm, more preferably 20 and 75 μm, more preferably between 25 and 50 μm.

A person of ordinary skill will appreciate that elements of the aspects of the MSCs or the pharmaceutical composition for use in the treatment of atopic dermatitis or of the MSCs or the pharmaceutical composition for use as an immunomodulating agent as described above return in the aspect of the pharmaceutical composition of the invention. Consequently, all aspects of the present invention are related. All features and advantages as described in one of the aspects as described above, can relate to any of these aspects, even if they are described in conjunction with a specific aspect.

The MSCs or the pharmaceutical composition comprising MSCs for use according to the current invention, possibly together with further components as described above, will by preference be frozen in order to allow long-time storage of the MSCs or of the composition. Preferably the MSCs or composition will be frozen at low and constant temperature, such as a temperature below −20° C. These conditions allow a save storage of the MSCs or composition, and enable the MSCs to keep their biological and morphological characteristics, as well as their high cell viability during storage and once thawed.

In a more preferred embodiment, the MSCs or the pharmaceutical composition comprising MSCs for use according to the current invention can be stored for at least 6 months at a maximum temperature of −80° C., optionally in liquid nitrogen. A crucial factor in the freezing of the MSCs is a cryogenic medium, in particular comprising DMSO. DMSO prevents ice crystal formation in the medium during the freezing process, but may be toxic to the cells in high concentrations. In a preferred embodiment, the concentration of DMSO comprises up to 20%, more preferably up to 15%, more preferably the concentration of DMSO in the cryogen comprises 10%. The cryogenic medium further comprises low-glucose medium such as low glucose DMEM (Dulbecco's Modified Eagle Medium).

Afterwards, the MSCs or the pharmaceutical composition comprising MSCs for use according to the current invention are preferably thawed before administration at a temperature around room temperature, preferably at a temperature between 20° C. and 37° C., more preferably at a temperature between 25° C. and 37° C., and in a time span of maximal 20 minutes, preferably maximal 10 minutes, more preferably maximal 5 minutes.

Furthermore, the MSCs or composition is preferably administered within 2 minutes after thawing, in order to safeguard the vitality of the MSCs.

The invention is further described by the following non-limiting examples which further illustrate the invention, and are not intended to, nor should they be interpreted to, limit the scope of the invention.

EXAMPLES AND/OR DESCRIPTION OF FIGURES

The present invention will now be further exemplified with reference to the following examples. The present invention is in no way limited to the given examples.

Example 1: Feasibility Study in Client Owned Dogs with Atopic Dermatitis

Set-up:

The objective of this study is to evaluate the feasibility of a single intravenous injection of ePB-MSCs (equine peripheral-blood derived MSCs) as treatment for dogs suffering from atopic dermatitis.

Isolation and Cultivation of ePB-MSCs

According to previously described methods, the ePB-MSCs are isolated from venous blood collected from the vena jugularis of one donor horse. Prior to cultivation of the ePB-MSCs, serum is tested for the presence of multiple transmittable diseases as described by Broeckx et al. 2012. Subsequently the stem cells are cultivated in a Good manufacturing practice (GMP)-certified production site according to GMP-guidelines until passage (P) 5 and characterized on viability, morphology, presence of cell surface markers and population doubling time. Evaluation of the presence (Cluster of Differentiation CD29, CD44 and CD90) and absence (Major Histocompatibility Complex (MHC) II and CD45) of specific cell surface markers is accomplished by using flow cytometry as previously described (Spaas et al., 2013). However, the detailed expression and secretion pattern has been previously described in WO 2020/182935. The cell viability is assessed using trypan blue. Afterwards, the cells are further cultivated until P10, trypsinized and resuspended at a final concentration of 300.000 cells/mL in Dulbecco's Modified Eagle Medium (DMEM) low glucose with 10% dimethylsulfoxide (DMSO). The ePB-MSCs are stored at −80° C. in cryovials until further use. Sterility of the final product is tested by the absence of aerobic bacteria, anaerobic bacteria, fungi, endotoxins and mycoplasma.

Study

A total of 11 canine patients with naturally occurring atopic dermatitis are treated with ePB-MSCs in two veterinary practices. Patient inclusion is restricted by the following inclusion criteria: symptoms of canine atopic dermatitis at least 1 month prior to enrolment, a Canine Atopic Dermatitis Extent and Severity Index-04 (CADESI-04)-score of at least 10, a good general health status apart from the target disease, based on general physical examination on day 0 and medical history of at least 2 months prior to enrolment. Patients with following conditions and treatments are excluded from the study: dogs with seasonal dermatitis, except if the sensitive period is known and if not treated at the end of the sensitive period, an ongoing corticosteroid treatment, any condition, actual or anticipated, that the veterinarian feels would restrict or limit the patient's successful participation for the duration of the study (e. g. parasitic infestations such as worms, fleas, etc.).

A physical examination and evaluation of the medical history of at least 2 months prior to assessment are performed. Furthermore, the skin is assessed by scoring the CADESI-04 (see Table 2 below). All examinations are performed by an experienced veterinarian. If the animals meet the inclusion criteria and none of the exclusion criteria, they are IV injected with 300.000 ePB-MSCs. Following, the dogs are clinically evaluated by an experienced veterinarian at three follow-up evaluation points: day 28, day 56 and day 84. At the evaluation points, the effect of the treatment is investigated and scored by performing the CADESI-04 grading system. During every follow-up a general physical examination is performed. In between veterinary visits, the owner evaluates for abnormal behavior or adverse events daily and is asked to fill in an owner questionnaire concerning the appetite, activity, the level of comfort, the pruritis (using a pVAS scoring scheme), redness of the skin and alopecia of the dog at home on day 0, 14, 42, 84 and 168.

Results:

Preliminary results of the CADESI-04 scoring post-treatment of the different treated dogs are presented in Table 2. Dog number 1 to 3 were treated with a subpotent batch. The immunomodulation was assessed by MLR as described in the "Detailed description of the invention", however this particular batch was unable to sufficiently suppress the proliferation of stimulated PBMCs. This also translated to the clinical efficacy, where we saw that 2 out of 3 dogs, did not respond to the treatment. As such, these dogs are left out of the efficacy assessment of potent ePB-MSCs.

When assessing the efficacy of potent ePB-MSCs, the results show an improvement of CADESI score of at least 45% at day 28 for 5 out of 8 dogs treated with ePB-MSCs (mean improvement of 38.27%; reduction of CADESI-04 with >50% in 50% (4 out of the 8 included dogs)). Furthermore, according to the owner questionnaire, the pVAS score has a relative decrease of at least 20% in 60% of the patients at day 14 (info available on 5 dogs). On day 28 the PVAS was assessed optionally. There was a relative decrease of at least 50% in 4 out of 5 dogs for which the PVAS score was available.

Conclusions:

In conclusion, IV injection with 300.000 ePB-MSCs is an effective therapeutic in the treatment of canine atopic dermatitis. Preliminary results show a beneficial effect on both pruritis, as well as the typical skin lesions associated with the disease in most of the treated dogs.

TABLE 2

CADESI-04 scoring per animal for different evaluation time points.

| Dog number | CADESI-score | | | |
|---|---|---|---|---|
| | day 0 | day 28 | day 56 | day 84 |
| 1 | 46 | 39 | 46 | 26[1]* |
| 2 | 16 | 13 | * | * |
| 3 | 12 | 2 | * | * |
| 4 | 31 | 9 | ○ | ○ |
| 5 | 15 | 0 | ○ | ○ |
| 6 | 18 | 37 | (PM* on day 35) 41 | * |
| 7 | 26 | 14 | 10 | 6 |
| 8 | 43 | 13 | ○ | ○ |
| 9 | 42 | 40 | 17 | 7 |
| 10 | 45 | 34 | 2 | 20 |
| 11 | 23 | 3 | 3 | 2 |

[1]Dog was started on apoquel in between visits, this score is this not reliable for the assessment of the efficacy of the ePB-MSCs
*premature removal due to target disease
○premature removal due to owner compliance Example 2: Feasibility Study in Client Owned Cats with Atopic Dermatitis Set-Up:

The objective of this study is to evaluate the feasibility of a single intravenous injection of ePB-MSCs (equine peripheral-blood derived MSCs) as treatment for cats suffering from atopic dermatitis.

Isolation and cultivation of ePB-MSCs is performed as described in Example 1 above.

Study

Feline patients with naturally occurring atopic dermatitis are treated with ePB-MSCs in veterinary practices. Atopic dermatitis is diagnosed based on the clinical diagnostic criteria of Favrot et al. (doi.org/10.1111/j.1365-3164.2011.01006.x). Each animal meets at least 6 of Favrot's diagnostic criteria. All included animals have a good general health status apart from the target disease, based on general physical examination on day 0 and medical history of at least 2 months prior to enrolment. Other pruritic diseases are ruled out based on trichoscopic examination, skin scraping, and cytology. Hypersensitivity to flea bites and food allergies are excluded by appropriate anti-flea medications and a strict 8-week elimination diet, respectively. Patients with following conditions and treatments are excluded from the study: an ongoing corticosteroid treatment, any condition, actual or anticipated, that the veterinarian feels would restrict or limit the patient's successful participation for the duration of the study (e. g. parasitic infestations such as worms, fleas, etc.).

A physical examination and evaluation of the medical history of at least 2 months prior to assessment are performed. Furthermore, the skin is assessed by scoring the FeDESI score. All examinations are performed by an experienced veterinarian. If the animals meet the inclusion criteria and none of the exclusion criteria, they are IV injected with 300.000 ePB-MSCs. Following, the cats are clinically evaluated by an experienced veterinarian at three follow-up evaluation points: day 28, day 56 and day 84. At the evaluation points, the effect of the treatment is investigated and scored by performing the FeDESI grading system. During every follow-up a general physical examination is performed. In between veterinary visits, the owner evaluates for abnormal behavior or adverse events daily and is asked to fill in an owner questionnaire (dual feline pVAS scoring scheme) concerning the pruritis of the cat at home on day 0, 14, 42, 84 and 168.

Results:

The preliminary results show an improvement of FeDESI score at day 28 for 13 out of 16 cats treated with ePB-MSCs. Furthermore, according to the owner questionnaire, the pVAS score has decreased in the majority of the cats patients at day 28.

Conclusions:

In conclusion, IV injection with 300.000 ePB-MSCs is an effective therapeutic in the treatment of feline atopic dermatitis. Preliminary results show a beneficial effect on both pruritis, as well as the typical skin lesions associated with the disease in most of the treated cats.

Figure 1B:
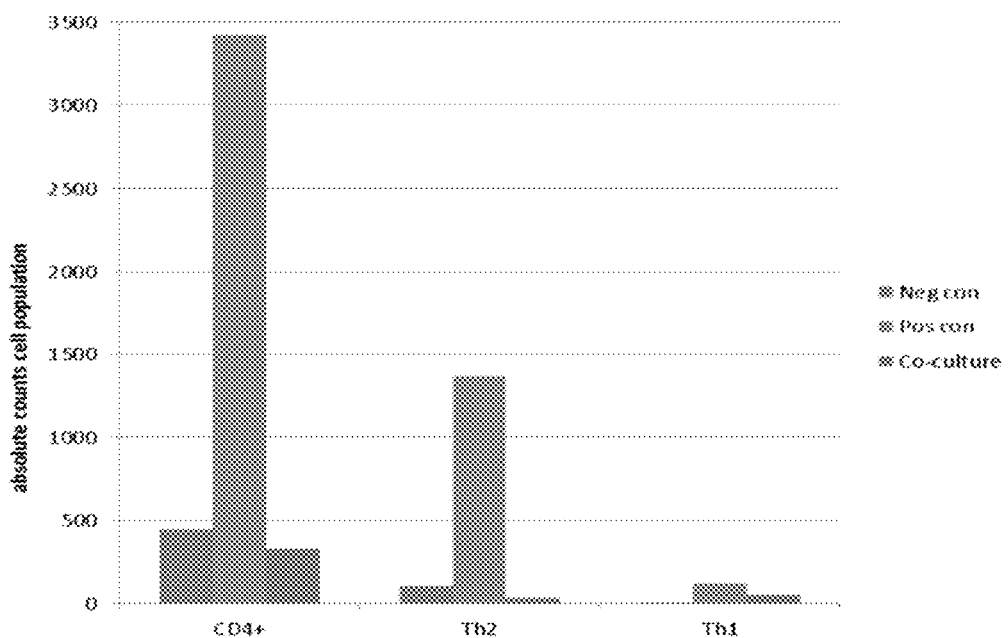
Figure 2:
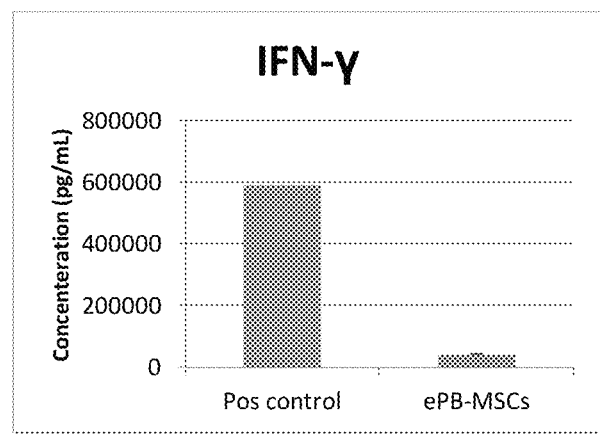
FIG. 2 shows the concentration of IFN-γ in supernatants of an MLR-test for positive control and co-cultured samples with ePB-MSCs.
Figure 3:
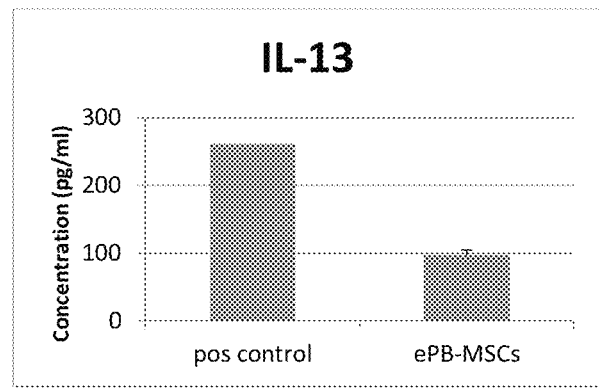
FIG. 3 shows the concentration of IL-13 in supernatants of an MLR-test for positive control and co-cultured samples with ePB-MSCs.

Example 3: Mixed Lymphocyte Reaction (MLR) in Dogs Before and After Treatment with ePB-MSCs Set-Up:

During the acute-phase of canine atopic dermatitis (cAD) the atopic inflammation is mainly driven by an increased T-helper 2 expression and is shifted towards an increase in both T-helper 2 (Th2) and T-helper 1 (Th1) in the chronic stage of the disease. In order to further investigate the mode of action of ePB-MSCs in the treatment of canine atopic dermatitis, the effect of ePB-MSCs on the canine T-helper subset 1 and 2 expression was investigated in vitro using the mixed lymphocyte reaction (MLR) assay. An MLR assay was set-up with ePB-MSCs co-incubated with concanavalin A (conA) stimulated canine peripheral blood mononuclear cells (PBMCs). After 4 days of co-incubation, the PBMCs were stained against the extra cellular markers to evaluate the specific expression of Th1 and Th2 in the proliferated PBMCs population using flow cytometry. In addition, two ELISA assays using commercially available kits for IFN-γ and IL-13 were performed on the supernatants of the positive control and co-culture samples of the MLR assay. These are both cytokines secreted by Th1 and Th2, respectively, and will be used to support the T-subset analysis Results:

Results of the MLR assay combined with T-helper subset analysis shows a decrease in absolute expression of proliferated $CD4^+$ cells, more specific the Th1 and Th2 population, in the co-cultured samples compared to the positive control (FIG. 1B). This decrease is further supported by the results of the ELISA assays, showing a decrease in both IFN-γ (FIG. 2) and IL-13 (FIG. 3) in the supernatants of the co-cultured samples when compared to the positive control. Furthermore, when looked at the relative expression in this small population of proliferated PBMCs after co-incubation, the expression of Th2 population in the proliferated PBMCs population is decreased significantly after co-culturing compared to the positive control. In contrast, the Th1 population is increased after co-incubation compared to the positive control (FIG. 1A).

Conclusion:

In this in vitro experiment, the immunomodulation properties of ePB-MSCs are confirmed with a significant decrease in the absolute numbers of $CD4^+$ cells, more specific a decrease in the Th1 and Th2 subset of this population. These results indicate that ePB-MSCs immunomodulate both the Th1 and Th2 subset of the white blood cells which are heavily involved in both the acute and chronic phase of cAD. Furthermore, when looking at the relative numbers, a shift from Th2 towards a Th1 subset is induced. These results confirm the therapeutic potential of ePB-MSCs in the treatment of cAD and provide insights in the in vivo mode of action of the ePB-MSCs.

Example 4: Mixed Lymphocyte Reaction (MLR) in Healthy Cats

Set-Up:

In order to investigate the immunomodulatory properties of ePB (equine peripheral blood derived)-MSCs in cats, ten healthy cats are intravenously (IV) injected with a composition comprising $3 \times 10^5$ ePB-MSCs in DMEM low glucose and 10% DMSO, in a volume of 1 ml, according to an embodiment of the invention at three time points (T0, T1 and T2) with 2 weeks in between each injection. The ten healthy cats, 4 males and 6 females, are of different breeds, in particular European shorthair, European longhair and Maine Coon, with a mean age of 6±4 years old.

Isolation and Cultivation of ePB-MSCs

According to previously described methods, the ePB-MSCs are isolated from venous blood collected from the vena jugularis of one donor horse. Prior to cultivation of the ePB-MSCs, serum is tested for the presence of multiple transmittable diseases as described by Broeckx et al. 2012. Subsequently the stem cells are cultivated in a Good manufacturing practice (GMP)-certified production site according to GMP-guidelines until passage (P) 5 and characterized on viability, morphology, presence of cell surface markers and population doubling time. Evaluation of the presence (Cluster of Differentiation CD29, CD44 and CD90) and absence (Major Histocompatibility Complex (MHC) II and CD45) of specific cell surface markers is accomplished by using flow cytometry as previously described (Spaas et al., 2013). However, the detailed expression and secretion pattern has been previously described in WO 2020/182935. The cell viability is assessed using trypan blue. Afterwards, the cells are further cultivated until P10, trypsinized and resuspended at a final concentration of 300.000 cells/mL in Dulbecco's Modified Eagle Medium (DMEM) low glucose with 10% dimethylsulfoxide (DMSO). The ePB-MSCs are stored at −80° C. in cryovials until further use. Sterility of the final product is tested by the absence of aerobic bacteria, anaerobic bacteria, fungi, endotoxins and mycoplasma.

Study

All cats are daily inspected by the caretaker and undergo a full physical examination at day 0 (T0), week 2 (T1), week 4 (T2) and week 6 (T3) by a veterinarian consisting of the assessment of rectal temperature, heart rate, respiratory rate, mucosal membranes appearance and capillary refill time, together with a hematological and biochemical analysis.

Furthermore, a modified mixed lymphocyte reaction (MLR) is performed at T0 (before treatment administration) and T3 (two weeks after the last (third) treatment) with fresh peripheral blood mononuclear cells (PBMCs) from each individual cat. This assay investigates the immunomodulatory (via stimulated PBMCs) properties of ePB-MSCs. To stimulate PBMCs, they are co-incubated with concanavalin A (ConA).

At T0, T1 and T2, after general physical examination, cats were intravenously (i.v.) injected with $3 \times 10^5$ ePB-MSCs. After thawing the cryovial in the palm of a hand, the content was checked for transparency and clearness and the cell suspension was immediately injected using a 22G i.v. catheter.

During the MLR assay, the immunomodulatory properties of the ePB-MSCs are investigated by co-incubating these cells with concanavalin A (ConA) stimulated feline PBMCs for four days and assessing the proliferation of the feline PBMCs. Non-stimulated feline PBMCs or stimulated feline PBMCs are used as negative and positive control, respectively. Consequently, PBMC proliferation (%) is evaluated using flow cytometry using Carboxyfluorescein succinimidyl ester 7-aminoactinomycin D (CFSE-7AAD) labeling. This assay is performed before and after treatment for all cats.

For this, venous feline blood was collected in EDTA blood collection tubes from each individual cat and diluted with HBSS and layered upon an equal amount of Percoll density gradient. After centrifugation on Percoll, the interphase containing the PBMCs was collected. The PBMCs were washed 3 times. Next, PBMCs from each cat were brought to a concentration of $1\times10^6$ cells per mL. Then, the PBMCs were labeled with CFSE using 1 μL of CFSE solution per mL of PBMC cell suspension. The CFSE labeled PBMCs were washed and resuspended in MLR medium (DMEM supplemented with 20% FBS, 1% AB/AM (Antibiotics/Antimycotics) and 1% BME (B-mercaptoethanol) 100×) to a final concentration of $2\times10^6$ PBMCs per mL. Then, the ConA-solution was added to all the wells of the plates except for the negative control samples. Finally, PBMCs of the designated cats were added to the associated wells. After 4 days of incubation all samples were transferred to FACS tubes, centrifuged and stained with 7-AAD for flow cytometry analysis.
Results:

At both timepoints (T0 and T3), the proliferation of the co-cultured ePB-MSCs with stimulated feline PBMCs (T0: 12.6±10%, T3: 26.2±9.8%) is significantly higher compared to the associated negative control (T0: 3.4±2.7%, T3: 4.9±1.3%) (p-value=0.05 and 0.008, respectively). However, the proliferation of the co-culture is significantly lower than the positive control at baseline (79.7±4.7%) (p-value=0.008) and after treatment (83.2±5.7%) (p-value=0.008). No significant difference in mean PBMC proliferation can be found in the co-culture of ePB-MSCs with stimulated feline PBMCs after treatment (26.2±9.8%) compared to baseline (12.6±10%) (p-value=0.017) (FIG. 1).
Conclusion:

The results of current study confirm the immunomodulatory properties of ePB-MSCs on feline PBMCs. This indicates the xenogeneic ePB-MSCs can be used in the treatment of cats.

Example 5: Target Animal Safety: Dogs

In order to assess safety of the single and repeated IV administration of ePB-MSCs to dogs, several clinical safety parameters are assessed in the present Example.
Methods 48 healthy purpose-bred beagles are randomly assigned to receive an intravenous injection with either the test item (n=40) or the reference item (n=8). Dogs treated with the test item, receive $3\times10^5$ ePB-MSCs (1 mL) (n=8), $9\times10^5$ ePB-MSCs (3 mL) (n=8) and $15\times10^5$ ePB-MSCs (5 mL) (n=8) on day 0 (single injection treatment groups) or $3\times10^5$ ePB-MSCs (1 mL) (n=8) and $15\times10^5$ ePB-MSCs (5 mL) (n=8) on days 0, 42 and 84 (repeated injection treatment groups). Following injection, all dogs are evaluated for 252 days. All dogs undergo daily clinical observation to assess the occurrence of adverse events. Blood and urine samples are taken for haematological, coagulation and biochemical analysis. At the end of the study period, all animals are euthanized for a thorough necropsy and histology and to analyze the retention of ePB-MSCs.
Results No overt differences in clinical safety parameters are observed between the control group and the treatment groups. However, this is not associated with any adverse event and overall means are within reference range. None of the dogs show any clinical abnormalities during physical examinations, clinical and injection site observations. No significant decrease of body weight occurred. No adverse events related to the study medication are observed and none of the laboratory results indicates any overt abnormalities during the study. Based on literary research, abnormal findings (other than the reticulocytosis) throughout the study can be considered incidental and unrelated to the test item. No ectopic tissue is observed during necropsy and histopathologic evaluation. In addition, all (mild) abnormalities observed are unlikely to be related to the Test Item. PCR analysis found the eMSCs to be absent in the analyzed samples, indicating that the MSCs do not reside long term in the tissues or circulation.

CONCLUSION

The test item is shown to be safe for intravenous use/administration.

The present invention is in no way limited to the embodiments described in the examples and/or shown in the figures. On the contrary, methods according to the present invention may be realized in many different ways without departing from the scope of the invention.

The invention claimed is:

1. A method for treating atopic dermatitis (AD) in canines and/or felines, comprising intravenously administering mesenchymal stem cells (MSCs) or a pharmaceutical composition comprising a therapeutically effective amount of MSCs to said canines and/or felines, wherein said MSCs are xenogeneic MSCs derived from peripheral blood of a horse, and wherein a single dose of $10^5$-$10^7$ MSCs per canine or feline is administered.

2. The method according to claim 1, wherein said MSCs are native.

3. The method according to claim 1, wherein multiple doses are administered with each dose being administered at different time points.

4. The method according to claim 1, wherein one dosage of said composition has a volume of maximally about 5 ml.

5. The method according to claim 1, wherein said MSCs measure negative for MHC class II molecules and/or CD45.

6. The method according to claim 1, wherein said MSCs measure positive for mesenchymal markers CD29, CD44 and CD90 and measure negative for MHC class II molecules and CD45.

7. The method according to claim 1, wherein said MSCs secrete immunomodulatory prostaglandin E2 cytokine when present in an inflammatory environment or condition.

8. The method according to claim 1, wherein said MSCs have an increased secretion of at least one of the molecules chosen of IL-6, IL-10, TGF-β, NO, or a combination thereof; and/or a decreased secretion of IL-1 when present in an inflammatory environment or condition and compared to a cell having the same characteristics but not being subjected to said inflammatory environment or condition.

9. The method according to claim 1, wherein said MSCs stimulate the expression of PgE2, IL-6, IL-10, NO, or a combination thereof when in the presence of PBMCs and/or suppress the secretion of TNF-α, IFN-γ, IL-1, TGF-β, IL-13 or a combination thereof when in the presence of PBMCs.

10. The method according to claim 1, wherein the MSCs are present in a sterile liquid.

11. The method according to claim 1, wherein the composition further comprises components selected from the group consisting of platelet-rich plasma (PRP), hyaluronic acid, compositions based on hyaluronic acid, glycosaminoglycans, or compositions based on glycosaminoglycans or any combination thereof.

12. The method according to claim 1, wherein said treatment is the treatment of AD-associated clinical and/or histopathological symptoms in canines and/or felines diagnosed with or suffering from atopic dermatitis.

13. The method according to claim 12, wherein said clinical symptom is pruritus and wherein the severity degree of said pruritus is evaluated using a Pruritis Visual Analog Scale (pVAS) scoring scheme.

14. The method according to claim 13, wherein said canine or feline has a pVAS score of at least 1 prior to administration of the MSCs or the pharmaceutical composition comprising MSCs and, after one or more administrations of the MSCs or the pharmaceutical composition comprising MSCs, said pVAS score has a relative decrease of at least 20% within a period of 1 month in at least 35% of the canines or felines treated with the MSCs or the pharmaceutical composition comprising MSCs.

15. The method according to claim 12, wherein said clinical symptom comprises AD-associated skin lesions and wherein the severity degree of said skin lesions is evaluated by calculating a skin lesion score using a skin lesion scoring scheme, wherein the skin lesion scoring scheme is a Canine Atopic Dermatitis Extent and Severity Index (CADESI)-04 scoring scheme in canines, and wherein the skin lesion scoring scheme is a SCORing Feline Allergic Dermatitis (SCORFAD) or Feline Extent and Severity Index (FeDESI) scoring scheme in felines.

16. The method according to claim 15, wherein the canines or felines suffering from AD have a skin lesion score of at least 10 prior to administration of the MSCs or the pharmaceutical composition comprising MSCs and, after one or more administrations of the MSCs or the pharmaceutical composition comprising MSCs, said score has a relative decrease of at least 25% in at least 35% of the canines or felines treated with the MSCs or the pharmaceutical composition comprising MSCs within a period of 1 month.

17. The method according to claim 12, wherein said histopathological symptom comprises lymphocytic perivascular dermatitis with infiltrating T cells in skin lesions.

18. A method for treating canines and/or felines diagnosed with or suffering from atopic dermatitis (AD) during the acute and/or the chronic phase of the AD inflammatory reaction, comprising intravenously administering a single dose of an immunomodulating agent, wherein said immunomodulating agent comprises MSCs or a pharmaceutical composition comprising a therapeutically effective amount of MSCs, wherein said MSCs are xenogeneic MSCs and are derived from peripheral blood of a horse, and wherein a dose of $10^5$-$10^7$ MSCs per canine or feline is administered.

* * * * *